United States Patent [19]

Michael

[11] 4,390,870
[45] Jun. 28, 1983

[54] INTERFACE CIRCUIT FOR BRUSH WEAR INDICATOR APPLICATION

[75] Inventor: Richard N. Michael, McKean, Pa.

[73] Assignee: General Electric Company, Research Triangle Park, N.C.

[21] Appl. No.: 273,555

[22] Filed: Jun. 15, 1981

[51] Int. Cl.³ .................. G08B 21/00; H02H 7/08
[52] U.S. Cl. ........................... 340/648; 307/116; 310/245; 340/531; 340/679; 361/23
[58] Field of Search .............. 340/679, 648, 531, 521; 200/61.4, 61.41; 310/245; 361/1, 23, 24; 307/116, 126, 130

[56] References Cited

U.S. PATENT DOCUMENTS

| | | | |
|---|---|---|---|
| 3,523,288 | 8/1970 | Thompson | 340/648 |
| 3,611,036 | 10/1971 | Edson | 340/648 X |
| 3,696,364 | 10/1972 | Lavelle | 340/531 |
| 3,854,089 | 12/1974 | Emler | 324/96 |
| 4,024,525 | 5/1977 | Baumgartner et al. | 340/648 |
| 4,027,204 | 5/1977 | Norbeck | 361/1 |
| 4,079,432 | 3/1978 | Godfrey | 361/23 |
| 4,333,095 | 6/1982 | Silva | 340/648 X |

Primary Examiner—John W. Caldwell, Sr.
Assistant Examiner—Joseph E. Nowicki
Attorney, Agent, or Firm—I. M. Freedman; V. P. Myles

[57] ABSTRACT

An interface circuit for use between a plurality of sensors, such as brush wear detecting sensors, and a single indicating alarm. The interface circuit is operable to transmit a signal from any or all of the sensors to actuate the alarm and latch it in its operative state until the alarm is de-energized by an operator.

6 Claims, 1 Drawing Figure

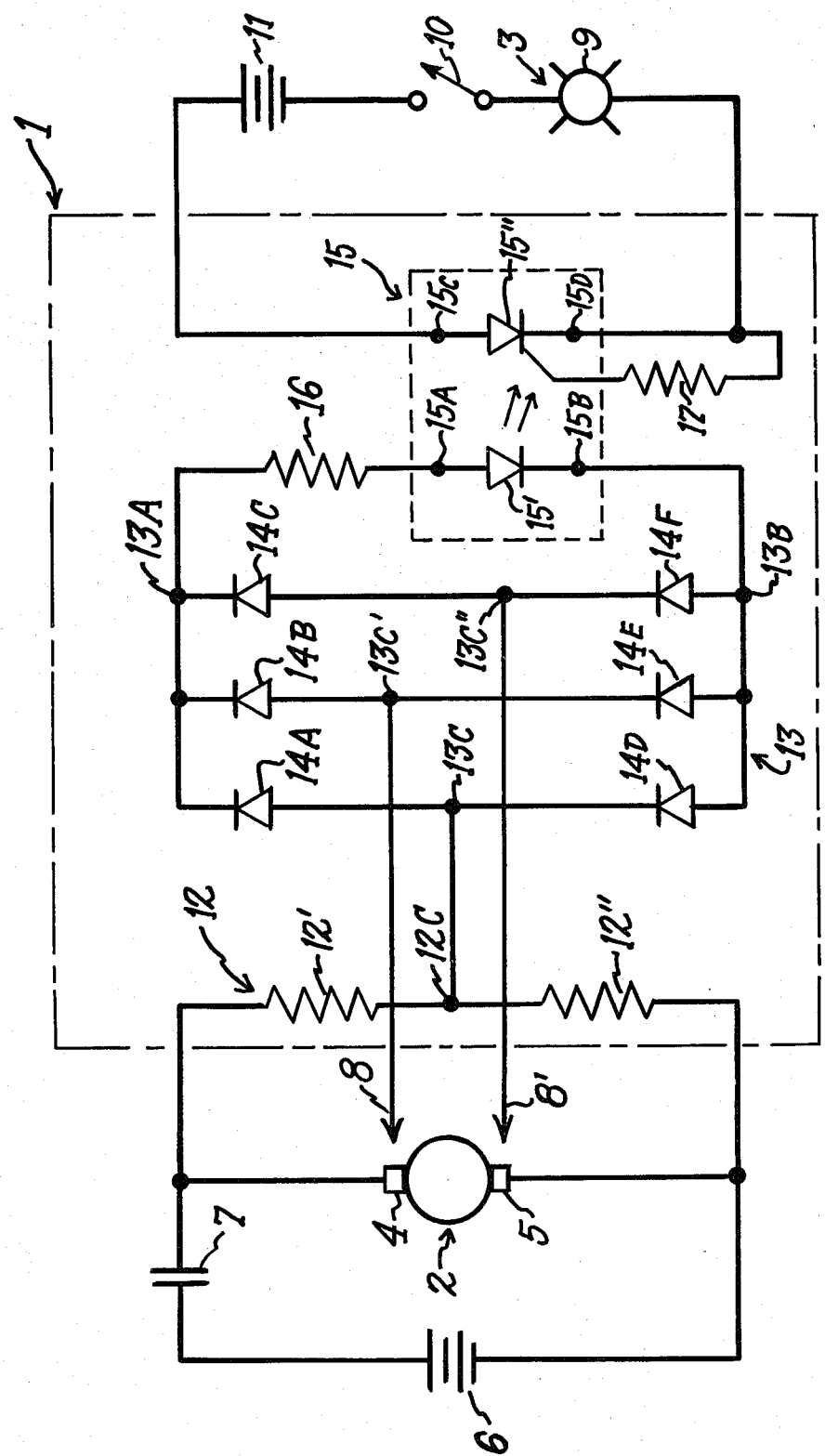

INTERFACE CIRCUIT FOR BRUSH WEAR INDICATOR APPLICATION

BACKGROUND OF THE INVENTION

The invention relates to an electrical interface circuit for isolating a plurality of monitored voltage inputs from an indicating circuit and, more particularly, relates to an interface circuit for use between a brush wear indicating circuit and a plurality of brush wear sensors.

The use of various sensor devices and indicating circuits to monitor and signal the occurrence of given degrees of brush wear, as such wear occurs during operation of a dynamoelectric machine containing such brushes was generally well-known before the present invention. A number of different types of such brush wear indicator devices are disclosed, for example, in my co-pending U.S. Patent Application Ser. No. 06/183,920, which was filed on Sept. 4, 1980 and is assigned to the assignee of the present invention. Moreover, a number of earlier brush wear indicating devices were described in several of the patents referred to in that co-pending application. Further specific examples of known prior art brush wear indicating sensor devices will be given below in conjunction with the description of the present invention in order to fully explain the best mode of its operation now known to the inventor.

In addition to the large number of different types of brush wear indicating devices known in the prior art, there presently exists a considerable number of different forms of indicating or alarm circuits which have been found to be particularly suitable for use with brush wear indicator devices. Several such circuits are shown, for example, in U.S. Pat. No. 3,523,288, which issued on Aug. 4, 1970. As is explained in the disclosure of that patent, it is generally well-known to provide brush wear indicating circuits that provide either normally-on, or normally-off indicating alarm means that are switched from one state to another responsive to the occurrence of a predetermined degree of brush wear in a monitored brush.

Another U.S. Pat. No. 4,024,525, which issued May 17, 1977 discloses a brush wear indicator circuit that is operable to simultaneously monitor wear occurring in a plurality of brushes, and to indicate the occurrence of a predetermined degree of such wear on one or more of the brushes by actuating a single indicator light or alarm signal. Selective actuation of the indicator light is controlled by a control circuit connected between brush wear sensor probes and the indicator light.

A common problem encountered in the application of presently known brush wear indicator devices and associated indicating alarms or signal circuits is that the input signals transmitted to the indicating circuits are often unreliable or include undesirably wide swings of input voltage. In addition, many prior art brush wear indicator devices are limited by their nature to utilization of current conducted through a monitored brush. Such brush currents often become very erratic when the brush wears sufficiently to cause it to have uneven contact with a commutator on which the brush is riding. Moreover, in brush wear indicator circuits that rely on a monitored brush voltage to actuate an indicating signal, either voltage-sensitive components in the coupling circuit between the brush wear sensor and the indicating circuit, or the indicator signal means itself may be damaged due to peaks of high voltage occurring on the monitored brushes. In view of these common problems with some of the prior art brush wear indicator devices and circuits, it is desirable to provide an interface circuit for use between brush wear sensor devices and brush wear indicating circuits to provide an efficient and reliable means for both manufacturing new brush wear indicator systems and for retrofitting existing brush wear indicator systems to avoid some of those problems.

OBJECTS OF THE INVENTION

Accordingly, it is a primary object of the present invention to provide an interface circuit for use between a plurality of brush wear sensors and an indicating circuit having a single alarm, which interface circuit avoids the above-noted problems of known prior art brush wear indicator devices and associated circuits.

Another object of the invention is to provide an interface circuit for use between a plurality of brush wear sensors and an indicating circuit in order to effectively isolate the indicator circuit from potentially damaging voltage surges that may occur on brushes monitored by the sensor devices.

A further object of the invention is to provide an interface circuit that is useful with a wide variety of different brush wear sensor devices and a variety of different indicating alarm circuits to provide a means for safely and reliably operating any one of such alarm circuits from the input of any of the suitably connected brush wear indicator devices.

Yet another object of the invention is to provide an interface circuit that is operable to latch a signal in its indicating condition responsive to one or more of a plurality of brush wear sensors providing an imput signal to the interface circuit. The latching feature of the circuit is independent of power supplied to, or removed from, brushes being monitored by the brush wear sensors.

Further objects and advantages of the invention will become apparent to those skilled in the art from the description of it presented herein considered in conjunction with the accompanying drawings.

SUMMARY OF THE INVENTION

In one preferred form of the invention, an interface circuit is provided which is useful for actuating a single alarm circuit responsive to an input signal from one or more of a plurality of brush wear indicator devices that are operably associated with brushes on a dynamoelectric machine such as a direct current motor. The interface circuit is characterized by including a photon coupled isolator having its output connected to the indicator alarm circuit and having its input connected to the output of a diode bridge circuit that has a plurality of input connections. Two of the input connections to the diode bridge are connected, respectively, to brush wear sensors and another of the diode bridge connections is connected to a voltage mid-point of a resistor bridge that includes connections adapted to be connected in series with the pair of brushes being monitored by the brush wear sensors. The interface circuit is operable to actuate a single alarm in the indicator circuit responsive to either or both of the brush wear sensors generating or transmitting a signal corresponding to the occurrence of a predetermined degree of brush wear on either or both of the brushes associated with the sensor devices. Once actuated, the alarm is latched "on" and remains actuated even if power is removed from the brushes being monitored by the wear-indicating devices. Additional brush wear sensors can be readily accommodated by simply adding a pair of diodes to the diode bridge for each such additional sensor and connecting the added sensor to a point between the added diodes.

DESCRIPTION OF THE DRAWINGS

The single FIGURE of the drawing is a circuit diagram including schematically illustrated circuit components and brush wear sensor devices electrically connected to illustrate the best mode of the interface circuit of the invention, shown in relation to a direct current motor having a plurality of brushes each of which is monitored by an associated brush wear sensor, and further shown in operative relation to a single indicating alarm circuit for signalling the occurrence of a predetermined degree of brush wear detected by one or all of the brush wear sensors.

BRIEF DESCRIPTION OF THE PREFERRED EMBODIMENTS

The preferred embodiment of the invention is described here with reference to the sole FIGURE of the drawing, which illustrates within the dashed line an interface circuit 1 constructed according to the invention. To facilitate an understanding of the invention, the interface circuit 1 is shown arranged in operative relationship with respect to a direct current motor 2 and an indicating circuit 3. In the arrangement shown, the interface circuit 1 is operable to transmit signals from brush wear sensors mounted in operative relationship to the respective brushes of the motor 2 in order to actuate an alarm, such as a signal light, in the indicating circuit 3.

Obviously, many different types of dynamoelectric machines and associated current conducting brushes can be used in combination with the interface circuit 1 of the invention. Likewise, a variety of different forms of indicating circuits, such as the circuit 3, will find application with the interface circuit of the invention. Accordingly, only the simplified schematic illustrations of the motor 2 and its associated controls, power source and brush wear sensors are presented in the drawing, and a similarly simplified indicating circuit 3 is depicted. Those skilled in the art will recognize that alternative types of circuits and devices may be used in lieu of those specifically described, in combination with the interface circuit of the invention. As illustrated in FIG. 1, the DC machine 2 comprises a schematically depicted conventional electric motor having a pair of conventional carbon-compound current conducting brushes 4 and 5 that are operatively connected in combination with a suitable source of direct current power 6, schematically illustrated as a battery. A suitable conventional motor controller 7 is shown in that series circuit to complete one well-known type of schematic DC motor circuit.

A pair of brush wear sensors 8 and 8' not mounted, respectively, in association with the brushes 4 and 5 of the motor to provide a means for producing or transmitting an electric signal responsive to one or both of the brushes experiencing a predetermined degree of wear. Preferably the brush wear sensors 8 and 8' are identical in configuration, but it will be recognized that different forms of sensors can be used in practicing the invention in any particular application, in order to achieve desired objectives other than the economies of standardization and simplified maintenance and operation. In the embodiment of the invention being described, the brush wear sensors each comprise an insulated electrical conductor embedded in each of the brushes, substantially parallel to the longitudinal axis of the respective brushes 4 and 5. In operation, when the brushes wear to a predetermined degree, the innermost end of one (or both) of the embedded conductor is forced into electrical conducting relationship with the commutator of the DC motor 2 as the insulation around the embedded conductor is worn away as a adjunct of such brush wear. The occurrence of such a degree of brush wear causes signal current to pass through the embedded conductor from which it is transmitted by the associated brush wear sensor (8 or 8') to the interface circuit 1, as will be described below.

Before considering the characteristic features of the interface circuit 1, the simplified indicating circuit 3 shown in the drawing will be briefly described. In the form shown, the indicating circuit 3 includes an alarm lamp 9 electrically connected in series with a manually operable switch 10 and a secondary source of power 11 that is effective to illuminate the lamp 9 when connected in a closed series loop with it. It will be apparent that the indicating alarm for the indicating circuit 3 need not be a lamp, but may be an audible horn, bell or other conventional type of signal annunciator, the actuation of which can be determined by operation of the interface circuit 1, in a manner analogous to that in which the indicating light 3 is operated, as will be described in detail below. It will also be apparent to those skilled in the art that the indicating circuit 3 need not include a switch such as the switch 10, or an auxiliary source of power, such as the battery 11, in order to function with the interface circuit 1 of the invention to provide suitable indicating alarms in alternative applications of the invention. However, the depicted form of indicating circuit 3 is useful in understanding the present invention, because it helps explain one advantage of the invention; namely, that it can be used to actuate an indicating signal that is energized either by power derived from the commutator current of a monitored machine, or that it can be actuated by a separate source of power which is entirely isolated from such a monitored machine. Furthermore, with such a separate power supply for the indicating alarm, the alarm will remain actuated, due to the latching operation of SCR 15", once an input signal from any of the brush wear sensors renders the SCR conductive.

Now that the motor 2 and its associated brush wear sensors 8 and 8' and the other relatively conventional motor control circuit has been explained, and a suitable simplified indicating circuit 3 has been described, the preferred embodiment of the circuitry for the interface circuit 1 of the invention will be explained. In the form of the interface circuit 1 depicted in the drawing, it comprises a resistor bridge circuit 12 including a first resistor 12' a second resistor 12" and a mid-point voltage connection 12C. A conventional diode bridge circuit 13 having a plurality of input connections 13C, 13C' and 13C" and a pair of output connections 13A and 13B is shown and includes the six diodes 14A-14F connected as shown between the pair of output connections 13A-13B and the three input connections 13C, 13C' and 13C". At this point, it should be recognized that additional brush wear sensors can be readily accommodated by the circuit 1, by simply adding an additional pair of diodes (not shown), connected as the illustrated diode pairs are, between points 13A and 13B, for each such additional sensor. Of course, a suitable connection, such as those shown at 13C' and 13C" would also be made from a mid-point of the conductor between the added diode pair and the added sensor. With such modifications, the circuit 1 can be used to monitor 4, 6 or more brushes on a single machine, or may be used to monitor brushes on several different machines.

Finally, the interface circuit 1 includes a photon coupled isolator 15 that has its input terminals 15A and 15B electrically connected, respectively, to the output connections 13A and 13B of the diode bridge. As shown in the drawing, a suitable current limiting means, such as resistor 16, is connected in series with the input terminals 15A and 15B of the isolator to protect its components from overcurrent damage. Of course, in alternative embodiments the resistor 16 could be replaced with a field effect diode, or other suitable essentially constant current device to afford the desired current limiting function. Output terminals 15C and 15D of the isolator 15 are electrically connected to transmit a signal to a suitable associated indicating means, such as the indicating circuit 3, shown connected to these terminals in the drawing, responsive to actuation of the photon coupled isolator 15.

It should be understood that any of a variety of suitable commercially available coupled isolators may be used in the interface circuit 1 of the invention in place of the particular type of isolator 15 shown in the drawing. However, in this preferred embodiment of the invention, the isolator 15 is a type that is commercially available from General Electric Company under the designation GE H11C3. Such an isolator includes a photon emitting diode 15' mounted in operative relationship to an SCR 15", as shown in the drawing. In order to control the sensitivity of the actuation of the SCR 15" of the isolator 15, a biasing resistor 17 is electrically connected to the output circuit of the isolator 15, as shown in the drawing.

Although the interface circuit 1 of the invention will find desirable applications in a number of different combinations with other apparatus, in the preferred form of the invention illustrated in the drawing, the interface circuit 1 is connected in combination with a direct current machine 2 and its associated pair of brush wear sensors 8 and 8' so that the brushes 4 and 5 of the motor 2 are connected in series with the resistor bridge 12, thereby to develop a mid-point voltage from the brushes 4 and 5 applied at the mid-point voltage connection 12C and to the input connector 13C of the diode bridge 13. The brush wear sensors 8 and 8' are connected, respectively, to transmit signals to the other two input connections 13C' and 13C", respectively, of the diode bridge 13, at such time as either or both of the brush wear sensors detects a predetermined degree of wear of the brush (4 or 5) associated with the sensors (8 and 8'). This preferred combination includes a source of direct current power 6 that is operatively connected through the motor controller 7 to the motor 2 through the brushes 4 and 5.

Finally, the preferred combination of the invention illustrates in the drawing includes a suitable indicating circuit means 3 having an alarm 9, such as the depicted light or glow lamp, connected in series with the output terminals 15C and 15D of the photon coupled isolator 15. As mentioned above, in this form of the invention an auxiliary source of direct current power in the form of a battery 11 is electrically connected in series with a manually operated switch 10 and the indicating light 9 so that the light 9 is operable, responsive to actuation of the photon coupled isolator 15, to supply power to the alarm 9 when actuation of the isolator closes the battery and alarm circuit to form a series loop. Of course, the manually operated switch 10, which might be, for example, an ignition key switch on a battery operated truck in which the DC motor 2 is mounted, would be closed at the time the DC motor 2 is started, in order to prepare the indicating circuit 3 for operation.

An advantage of this preferred form of the invention is that the SCR 15" of the isolator 15 remains in a conducting state, until the switch 10 is opened; accordingly, the brush wear sensors 8 or 8' need not continue transmitting a signal, indicative of the occurrence of the above-mentioned predetermined degree of brush wear in either of the associated brushes 4 or 5, to either of the connection points 13C' or 13C" of the diode bridge. In fact, electric power can be removed from the brushes 4 and 5 after the alarm 9 has been actuated, and the SCR will continue to supply power to the alarm from the battery 11.

An initiating imput signal from the sensors 8 and 8' will operate the indicating alarm 9 regardless of whether the signals transmitted from the brush wear sensors are positive or negative in polarity as they reach the diode bridge connection points 13C' and 13C". Thus, it will be understood that even if only one of the sensors 8 or 8' transmits a signal indicative of the predetermined degree of brush wear, the alarm lamp 9 will be energized by actuation of the SCR 15" and the lamp will remain on until an operator terminates the alarm signal; normally by momentarily opening the switch 10 at the time that the worn brush or worn brushes are replaced.

From the description of the invention presented herein, it is believed that those skilled in the the art will recognize that various alternative forms of the invention and modificiations of the preferred embodiment of it described herein can be made without departing from the scope of the following claims; thus, it is my intention to encompass within those claims the true limits of the invention.

I claim:
1. An interface circuit for use between a brush wear indicating circuit and a plurality of brush wear sensors that are each operable respectively, to transmit or produce an electrical signal responsive to the occurrence of a predetermined degree of wear of an associated brush, comprising;
   a resistor bridge circuit having a midpoint voltage connection;
   a diode bridge circuit having a plurality of input connections and a pair of output connections, one of said input connections being electrically connected to the midpoint voltage connection of said resistor bridge, and each of the other input connections being connectable, respectively, to receive signals from one of said plurality of brush wear sensors,
   and a photon coupled isolator having input terminals electrically connected, respectively, to the output connections of said diode bridge and having output terminals electrically connectable to transmit a signal to an indicating means responsive to actuation of the photon coupled isolator.

2. An invention as defined in claim 1, including an SCR (15") in said photon coupling isolator and a biasing resistor electrically connected to one of said output terminals and to said SCR to control the sensitivity of actuation thereof.

3. An invention as defined in claim 2 including a current limiting means electrically connected in series with the input terminals of said photon coupled isolator.

4. An invention as defined in claim 1 in combination with a direct current machine having a plurality of current conducting brushes, and a plurality of brush wear sensors each operatively mounted, respectively, in association with one of said brushes, said brushes being connected in series with said resistor bridge, and said sensors being connected, respectively, to transmit signals to said other input connections of the diode bridge, responsive to any or all of said sensors detecting a predetermined degree of wear of the respective brushes associated therewith.

5. An invention as defined in claim 4 in combination with a source of direct current power operatively connected to said plurality of brushes to energize the machine, and wherein said indicating means comprises an alarm electrically connected in series with the output terminals of said photon coupled isolator, said alarm being operable responsive to actuation of said isolator to indicate the occurrence of a predetermined degree of wear of one or both of the brushes.

6. An invention as defined in claim 5 in combination with an auxilliary source of direct current electrically connected in series with said alarm and operable to supply power to said alarm when it is operated by actuation of said isolator, said photon coupled isolator including an SCR that remains latched in a conducting state to keep said alarm accuated until power from the auxilliary source to the SCR is interrupted.

* * * * *